United States Patent [19]

Rodwell et al.

[11] Patent Number: 4,671,958

[45] Date of Patent: Jun. 9, 1987

[54] ANTIBODY CONJUGATES FOR THE DELIVERY OF COMPOUNDS TO TARGET SITES

[75] Inventors: John D. Rodwell, Yardley; Thomas J. McKearn, Narberth, both of Pa.

[73] Assignee: Cytogen Corporation, Princeton, N.J.

[21] Appl. No.: 356,315

[22] Filed: Mar. 9, 1982

[51] Int. Cl.⁴ .................... A61K 39/00; A61K 37/00; A23J 37/00

[52] U.S. Cl. ........................................ 424/85; 514/2; 514/6; 514/8; 530/387; 530/388; 530/389; 530/390; 530/391; 530/828; 424/86; 424/87

[58] Field of Search ............................ 424/86, 85, 87; 260/112 R; 435/7, 12, 25, 177, 188, 192, 181; 514/2, 6; 530/387, 388, 389, 390, 391, 828

[56] References Cited

U.S. PATENT DOCUMENTS

| | | | |
|---|---|---|---|
| 3,970,521 | 7/1976 | Zaborsky et al. | 195/63 |
| 4,093,607 | 6/1977 | Sela et al. | 424/85 |
| 4,167,449 | 9/1979 | Gargiulo et al. | 435/16 |
| 4,217,338 | 8/1980 | Quash | 435/7 |
| 4,256,833 | 3/1981 | Ali et al. | 435/7 |
| 4,263,279 | 4/1983 | Sela et al. | 424/85 |
| 4,287,345 | 9/1981 | Kotani et al. | 446/261 |
| 4,419,444 | 12/1983 | Quash | 424/1 |

FOREIGN PATENT DOCUMENTS

1446536 2/1975 United Kingdom.

OTHER PUBLICATIONS

March *Advanced Organic Chem.*, 2nd ed., 1977, pp. 824–827.
Karush *Biochem.*, vol. 18(11), 1979, pp. 2226–2231, "Interaction of a Bivalent Ligand with IgM Anti-Lactive Antibody".
Gililand et al., *Proc. Natl. Acad. Sci., U.S.A.*, vol. 77, pp. 4539–4543 (1980).
Krolick et al., *Proc. Natl. Acad. Sci., U.S.A.*, vol. 77, pp. 5419–5423.
Thorpe et al., *Eur. J. Biochem.*, vol. 116, pp. 447–454 (1981).
Teijin K. K., Derwent Abstract No. 55398 (European Patent Office Application No. 55115).
Teijin K. K., Derwent Abstract No. 57670 (European Patent Office Application No. 55575).
Vogel et al., *Proc. Natl. Acad. Sci., U.S.A.*, vol. 78, pp. 7707–7711 (1981).
Hurwitz et al., *J. Appl. Biochem.*, vol. 2, pp. 25–35 (1980), "Soluble Macromolecules as Carriers for Dainorubicin".
Monsigny et al., *FEBS Letters*, vol. 119(1), Sep. 1980, "Preparation and Biological Properties of a Covalent Antitumor Drug-Carrier-Counter (PAC Conjugate)".

(List continued on next page.)

*Primary Examiner*—Thomas G. Wiseman
*Assistant Examiner*—Robin Teskin
*Attorney, Agent, or Firm*—Pennie & Edmonds

[57] ABSTRACT

A method is described for the covalent attachment of linker groups to specific sites on antibody molecules directed against any desired target antigen (tumor, bacterial, fungal, viral, parasitic etc.). These linkers can be attached via amide or ester bonds to compounds for delivery which contain available amino or hydroxy groups (e.g., bioactive agents, cytotoxic agents, dyes, fluors, radioactive compounds, etc.). In addition the linkers can be incorporated into insoluble matrices for use in separation schemes which are based upon antibody-antigen interactions.

The linkers may be designed so that they are susceptible to cleavage by any one of the serum complement enzymes. When prepared according to the methods described herein, the resulting modified antibody molecule retains the ability to bind antigen and to fix serum complement. Thus, when administered to a patient the antibody conjugate binds to its target in vivo. As a result of the subsequent activation of the patient's serum complement, the covalently attached compound will be specifically cleaved at the target site by the proteolytic enzymes of the complement system.

49 Claims, 7 Drawing Figures

OTHER PUBLICATIONS

Hobart et al., *The Immune System: A Course on the Molecular Cellular Basis of Immunity* Blackwell Scientific Publications, p. 37.
Blair and Ghose, 1983, J. of Immunological Methods 59; 129–43.
Kanellos et al., 1985, J. Nat'l Cancer Inst. 75; 319–32.
Scheinberg and Strand, 1983, Cancer Res. 43: 265–72.
Buchegger et al., 1983, J. Exp. Med. 158: 413–27.
Dorington and Klein, 1983 in Progress in Immunology, Y. Yamamura and T. Tada, eds., Academic Press, Inc., Tokyo, Japan, pp. 37–46.
Nose et al., 1983, Proc. Nat'l Acad. Sci. U.S.A. 80:6632–36.
Leatherbarrow et al., 1983, Molec. Immunol. 22: 407–15.
Bale et al., Cancer Research 40:2965–2972 (1980).
Bing, Biochemistry 8:4503–4510 (1969).
Blythman et al., Nature 290:145–146 (1981).
Caporale et al., J. Immunol. 126:1963–1965 (1981).
Cooper, Biochemistry 14:4245–4251 (1975).
Davis & Preston, Science 213:1385–1388 (1981).
Ghose et al., J. Natl. Cancer Inst. 61(3): 657–676 (1978).
Gregoriadis, Pharmac. Ther. 10:103–118 (1980).
Gregoriadis, Nature 265: 407–411 (1977).
Heath et al., Biochim. Biophys. Acta 640: 66–81 (1981).
Huang et al., J. Biol. Chem. 255(17): 8015–8018 (1980).
Hurwitz et al., Int. J. Cancer 24: 461–470 (1979).
Japan Patent Application Serial No. 71, 048/76; Ogura and Murayama.
Japan Patent Application Serial No. 63, 325/78 Ogura.
Leserman et al., Nature 288: 602–604 (1980).
Martin et al., Biochem. 20: 4229–4238 (1981).
Murayama et al., Immunochem. 15: 523–528 (1978).
Reid and Porter, Ann. Rev. Biochem. 50: 433–464 (1981).
Sim et al., Biochem. J. 163: 219–227 (1977).
United Kingdom Patent Application No. 7,906,506, Public Disclosure No. 6B 2,105,530 A.
Willan, et al., 1977, FEBS Lett. 80(1): 133–136.

ALKERAN

+ CH₃CH₂OH

↓ → H₂O

↓ +CBZ—gly—gly—arg
+ carbodiimide
→ H₂O

↓ acid

TRIPEPTIDE — ALKERAN

Unoxidized Antibody

Oxidized Antibody

ANTIBODY CONJUGATES FOR THE DELIVERY OF COMPOUNDS TO TARGET SITES

TABLE OF CONTENTS

1. FIELD OF THE INVENTION

2. BACKGROUND OF THE INVENTION

3. SUMMARY OF THE INVENTION

4. BRIEF DESCRIPTION OF FIGURES

5. DESCRIPTION OF THE INVENTION 5.1 Choice of Antibody and Compound of Interest 5.2 Serum Complement and Selection of Linkers 5.3 Methods for Attaching Compounds of Interest to Antibody Molecules 5.3.1 Attachment to Oxidized Carbohydrate Moieties of the Antibody Molecule 5.3.2 Attachment to Sulfhydryl Groups of the Antibody Molecule 5.3.3 Attachment to Amino or Carboxy Groups of the $F_c$ Region of the Antibody Molecule 6. EXAMPLES: A METHOD FOR COMPLEMENT-MEDIATED RELEASE OF ANTIBODY-TARGETED COMPOUNDS AT CELL SURFACES 6.1 Oxidation of the Carbohydrate Moiety of the Antibody Molecule 6.2 Preparation of Tripeptide-AMC for Attachment to the Antibody Molecule 6.3 Specific Covalent Attachment of Phenylhydrazide-Tripeptide-AMC to the Oxidized Carbohydrate Moiety of the Antibody Molecule 6.4 Complement Fixation Assays 6.4.1 Preparation of Human Complement 6.4.2 Hemolytic Assay for Complement Fixation 6.4.3 Non-Hemolytic Assay for Complement Mediated Release of AMC

1. FIELD OF THE INVENTION

This invention relates to the general area of carrier systems capable of delivering compounds to target sites in vivo or in vitro. Such systems include the general area of the delivery of pharmaceutical agents or other compounds to target sites in vivo, both in vitro and in vivo imaging systems (e.g., tumor imaging systems), in vitro assays, cell sorting systems and separation schemes based upon antigen-antibody interactions.

Finally, this invention also relates to the chemistry of linking compounds to antibody molecules so that neither the ability to bind antigen nor the subsequent activation of complement is impaired.

2. BACKGROUND OF THE INVENTION

A number of agents have been utilized as carrier molecules with limited success in drug delivery systems. In practice the carrier should be non-toxic and target site specific. Ideally there should be a mechanism for release of the active form of the compound from the carrier at the target site. Carrier molecules such as DNA, liposomes, proteins, steroid hormones, and antibodies (whole antibody molecules or Fab fragments) have been used in conjunction with a broad spectrum of pharmaceutical or cytotoxic agents such as: radioactive compounds (e.g., $I^{125}$, $I^{131}$); agents which bind DNA, for instance, alkylating agents or various antibiotics (e.g., daunomycin, adriamycin, chlorambucil); antimetabolites such as methotrexate; agents which act on cell surfaces (e.g., venom phospholipases and microbial toxins); and protein synthesis inhibitors (e.g., diphtheria toxin and toxic plant proteins). For reviews on the subject see Bale et al., 1980, Cancer Research 40: 2965–2972; Ghose and Blair, 1978, J. Natl. Cancer Inst. 61(3): 657–676; Gregoriadis, 1977, Nature 265: 407–411; Gregoriadis, 1980, Pharmac. Ther. 10: 103–118; Trouet et al., 1980, Recent Results Cancer Res. 75: 229–235. Some of the delivery systems which are more pertinent to the present invention are discussed below.

Liposome mediated delivery of pharmaceutical agents has major drawbacks because of its lack of target specificity. Recently, investigators have attempted to overcome this problem by covalently attaching whole antibody or Fab fragments to liposomes containing a pharmaceutical agent (Heath et al., 1981, Biochim. Biophys. Acta 640: 66–81; Huang et al., 1980, J. Biol. Chem. 255(17): 8015–8018; Jansons and Mallet, 1981, Anal. Biochem. 111: 54–59, Martin et al., 1981, Biochem. 20: 4229–4238). Others have reported the coupling of protein A (Staph A protein) to liposomes in order to direct the preparation to multiple specific targets which have previously been bound to antibodies. Such targets are simply limited by the antibodies used (Leserman et al., 1980, Nature 288: 602–604). However, an intrinsic problem of particular importance in any lipsome carrier system is that in most cases the targeted liposome does not selectively reach its target site in vivo. Whether or not liposomes are coated with antibody molecules, liposomes are readily phagocytosed by macrophages and removed from circulation before reaching other target sites.

Most investigators have recognized another major problem inherent in the liposome targeting system, which is that binding of the targeted liposomes to the target cell does not ensure incorporation of the liposome contents, hence, the pharmaceutical agent, into the target cell (Weinstein et al., 1978, Biochim. Biophys. Acta 509: 272–288). A few investigators have tried to overcome this problem by targeting liposomes using receptor specific compounds which would be internalized into the target cell (Leserman et al., 1980, Proc. Natl. Acad. Sci. USA 77(7): 4089–4093; Mauk et al., 1980, Proc. Natl. Acad. Sci. USA 77(8): 4430–4434). The problem of internalizing the liposome contents still exists, however, because not all tumor cells are actively phagocytic. For instance, fibrosarcoma cells are much less phagocytic than are cells of lymphomas and leukemias. Thus, these liposome mediated delivery systems rely upon the ability of the target cell itself to internalize a substance which will be ultimately lethal to the cell.

Finally, if the liposome is internalized into the target cell, there is no assurance that the pharmaceutical agent will be released in its active form. After phagocytosis the liposome contents are packaged within lysosomes of the target cell. The array of proteolytic enzymes contained within the lysosome may either degrade the pharmaceutical agent or render the agent inactive by altering its structure or cleaving the active site. The variety of proteolytic enzymes contained in the lysosome makes it very difficult, if not impossible, to devise bonding arrangements that will allow release of the pharmaceutical agent in its active form. Thus, reliance upon the enzyme content of the target cell lysosomes is, at best, a haphazard system to effect release of the active form of the pharmaceutical agent.

A number of investigators have reported target systems involving attachment of pharmaceutical agents directly to conventional antibodies, monoclonal antibodies, or to Fab portions of antibodies directed against tumor antigens. See review articles, supra, and Blythman et al., 1981, Nature 290: 145-146; Davis and Preston, 1981, Science 213: 1385-1388; Hurwitz et al., 1979, Int. J. Cancer 24: 461-470); U.S. Pat. No. 4,093,607; and U.K. Pat. No. 1446536. Urdal and Hakomori (1980, J. Biol. Chem. 255(21): 10509-10579) describe an antibody targeted, avidin mediated, drug killing of tumor cells.

Other investigators are examining proteins other than antibodies as carriers in a target system. For example, desialylated glycoproteins are preferentially taken up by hepatocytes. See review articles, supra, and Bernstein et al., 1978, J. Natl. Cancer Inst. 60(2): 379-384.

The methods used by these investigators for binding the cytotoxic agents to the antibody molecule involve either non-covalent or covalent linkages. Since non-covalent bonds are more likely to be broken before the antibody complex reaches the target site, covalent linkages are preferred in these systems. For instance, carbodiimide has been used to link carboxy groups of the pharmaceutical agent to amino groups of the antibody molecule. Bifunctional agents such as dialdehydes or imidoesters have been used to link the amino group of a drug to amino groups of the antibody molecule. Some investigators have used the Schiff base reaction to link drugs to antibody molecules. This method involves the periodate oxidation of a drug or cytotoxic agent that contains a glycol or hydroxy group, thus forming an aldehyde which is then, reacted with the antibody molecule. Attachment occurs via formation of a Schiff base with amino groups of the antibody molecule. Additionally, drugs with reactive sulfhydryl groups have been coupled to antibody molecules. Isothiocyanate can be used as a coupling agent for covalently attaching compounds to antibodies. This method has been used to attach fluorescent compounds to antibody molecules for use in fluorescence microscopy (Brandtzaeg, 1973, Scand. J. Immunol. 2: 273-290) and cell sorting systems (Loken and Herzenberg, 1975, Annals N.Y. Acad. Sci. 254: 163-171).

Although the antibody carrier systems described above are more specific for the target than are the liposome carrier systems, a significant problem exists in the release of the pharmaceutical agent at the target site. As in the liposome mediated systems, the antibody-drug compounds must be internalized by the tumor cell so that the drug can be released through cleavage by lysosomal enzymes (see review articles, supra). Additionally, the nonspecific linkage of the pharmaceutical agent to random sites on the antibody molecule may interfere with antigen binding capacity, thus reducing the effectiveness of the system.

Radiopharmaceutical techniques currently used in non-invasive in vivo imaging methods are based upon the ability of the target organ to remove the radiopharmaceutical label from the circulation. These techniques utilize various substances to deliver radioactive compounds to desired targets; such substances include substrates, substrate analogs, ligands, hormones, radionuclides, bifunctional chelates (linker groups containing a chelator at one end which is able to bind a heavy metal or radionuclide and a reactive group at the other end which can covalently attach to a target cell) and liposomes (Spencer, R. P., ed. 1980. Radiopharmaceuticals Structure-Activity Relationship. Grune & Stratton, New York; Eckelman and Levanson, 1977, Intl. J. Appl. Radiation and Isotoper 28: 67-82). Other non-invasive techniques currently available are emission tomography, nuclear magnetic resonance imaging, and in vivo spectroscopy. See review article by Brownell et al., 1982, Science 215: 619-626 where the authors suggest the application of labeled antibodies in the field of radiopharmaceuticals.

3. SUMMARY OF THE INVENTION

This invention describes the use of antibodies as carrier molecules for the targeting of a compound or compounds for delivery (hereinafter referred to as "compound") to specific cells, tissues, organs, or any other site in vivo, or in vitro and the subsequent complement mediated release of the compound at the target site.

Antibodies directed against any desired target (e.g., antigenic determinants of tumor cells, virus, fungi bacteria, or parasites) may be used as carrier molecules. Although conventional antibodies may be used as carrier molecules, monoclonal antibodies offer the advantages of increased specificity for antigen and improved efficiency of the delivery system.

Once administered in vivo, the carrier antibody molecule will attach to the antigenic determinant of the target site. The subsequent release of the linked compound is dependent upon complement activation. Complement is the collective name for a group of serum proteins which are sequentially activated (the complement cascade) by the formation of certain immune complexes. Several of the complement components of the cascade have proteolytic activity which is specific for particular substrates or chemical bonds.

According to the process of the present invention, a compound is attached to an antibody carrier molecule of an immunoglobulin class that is capable of complement activation. This attachment is accomplished via linkers which are susceptible to cleavage by one or more of the activated complement enzymes, and one or more different compounds may be attached to each antibody molecule. The resulting antibody conjugate is administered to an individual. Subsequent to the binding of the modified antibody and antigen in vivo, the individual's serum complement is activated and the compounds will be selectively cleaved and released at the target site. Such conjugates may also be used for the in vitro detection and identification of target antigen in a complement-fixation assay system.

For the practice of this invention it is desirable to attach the compound to the antibody molecule without interfering with either the antigen binding capacity of the antibody, or with the ability to activate complement (also called complement fixation). The present invention describes the novel linkers and methods of attachment which may be used to attach compounds to any antibody capable of activating complement.

Alternatively, certain techniques, such as tumor imaging, or separation schemes based upon antigen-antibody interactions, wherein the antibodies are attached to an insoluble matrix, require that the compound remain attached to the target site. In an alternate embodiment, when cleavage at the target site is *not* desirable, then the linker group utilized is insensitive to the activated complement proteins, or the antibody molecule is of a class or type that does *not* activate complement.

Finally, for delivery of other compounds, e.g., hormones or neurotransmitters, where it may be desirable to cleave the compound without activation of the complement cascade, one may use a protease sensitive linker attached to an antibody that does not fix complement.

4. BRIEF DESCRIPTION OF FIGURES

FIG. 1 is a schematic representation of an antibody molecule or immunoglobulin of the IgG class (a), and of the IgM class (b).

FIG. 2 represents a portion of the complement cascade activated by the classical pathway. C1 through C9 represent complement proteins. The bar over certain numbers indicates an active enzyme. S' represents a site on the cell membrane.

Figure 7:
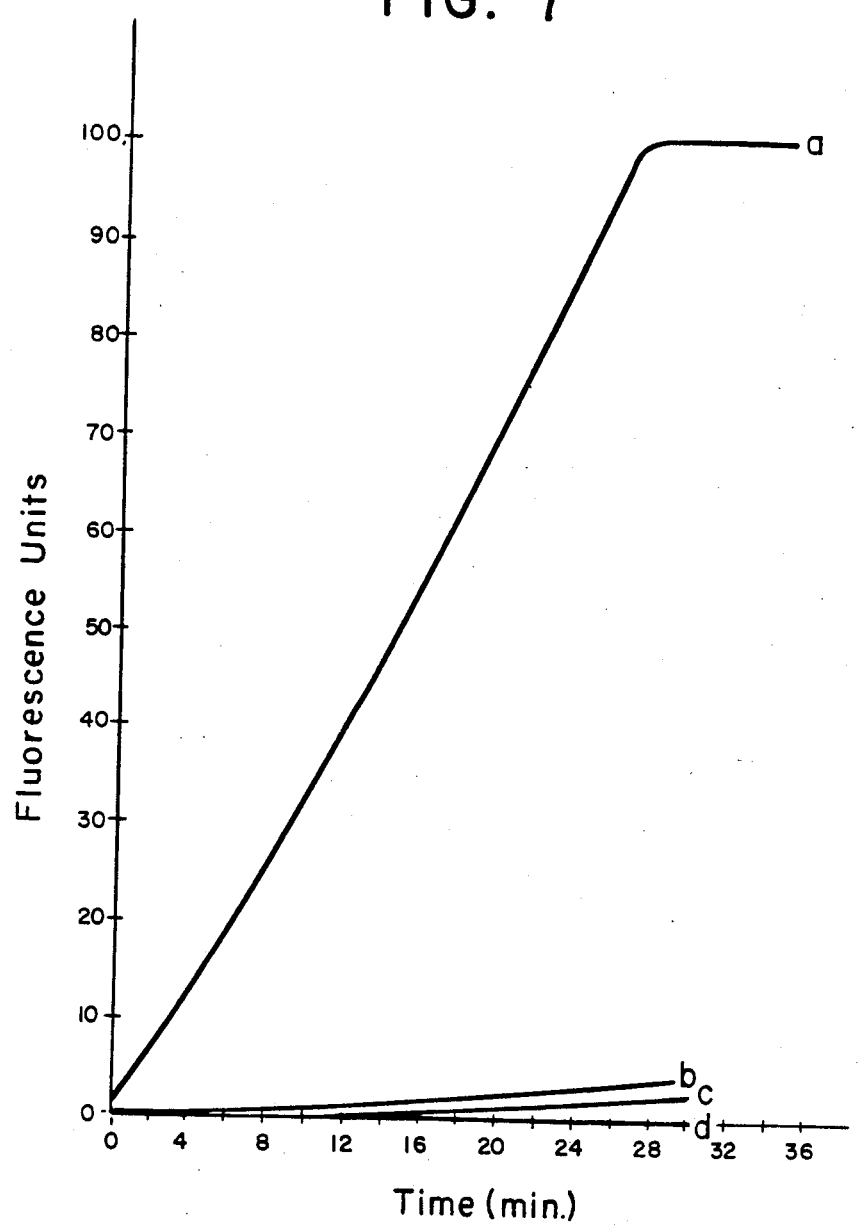

FIG. 7 represents the results of experiments showing the specific complement mediated release of AMC along with certain controls. Fluorescence is monitored at 460 nm with excitation at 380 nm. An increase in fluorescence indicates release of AMC from the Antibody-Phenylhydrazine-Tripeptide-AMC (APTA) conjugate; (a) represents APTA conjugate incubated with glutaraldehyde-fixed sheep red blood cells and human complement; (b) represents APTA conjugate incubated with glutaraldehyde-fixed rat red blood cells and human complement; (c) represents APTA conjugate incubated with glutaraldehyde-fixed sheep red blood cells; (d) represents APTA conjugate alone.

5. DESCRIPTION OF THE INVENTION

According to the method of the present invention, a compound is attached to an antibody directed against a target antigen. When release of the active form of the compound at the target site is desired, then the compound is attached to specific sites on an antibody molecule (immunoglobulin) belonging to a class that is capable of activating the complement cascade. This attachment is accomplished via chemical bonds (e.g., an ester or amide linkage) and linker groups (e.g., peptides or amino acids) which are susceptible to cleavage by one or more of the serum complement components.

The chemical linking methods described herein allow the resulting antibody conjugate to remain the ability to bind antigen and to activate the complement cascade. As a result, when the conjugate is administered to an individual, the subsequent formation of immune complexes with target antigens in vivo activates the individual's serum complement. If the linker is designed to be susceptible to cleavage by complement, the compound will be cleaved at the target site by one or more of the enzymes of the complement cascade. Since release of the compound occurs after delivery to the target site the efficiency of the target delivery system is greatly improved.

The method of the present invention offers another advantage over other targeting systems. It is known that all cells of a tumor do not each possess the target antigenic determinant. Thus, delivery systems which require internalization into the target cell will effect successful delivery only to those tumor cells that possess the antigenic determinant and that are capable of internalizing the complex. Tumor cells that do not possess the antigenic determinant or are incapable of internalization, will escape treatment.

According to the method of the present invention, antibody carrier molecules deliver the compound to the target cells. More importantly, however, once attached to the target cell, the method described in the present invention allows the release of the active compound by the individual's activated complement enzymes. Once released, the coupound is then free to permeate the target sites, e.g., tumor mass. As a result, the compound will act on tumor cells that do not possess the antigenic determinant as well as those tumor cells that do possess the determinant. Additionally, the entire process is not dependant upon internalization of the conjugate.

The method of targeted delivery described herein may be employed for a number of purposes. The choice of antibodies, linkers, and compounds used to make the conjugates depends upon the purpose of delivery. The delivery and release of pharmaceutical compounds at specific target sites may result in selectively killing or preventing the proliferation of tumor cells, cancer cells, fungi, bacteria, parasites, or virus. The targeted delivery of hormones, enzymes, or neurotransmitters to selected sites may also be accomplished. Ultimately the method of the present invention may have an application in gene therapy programs wherein DNA or specific genes may be delivered in vivo or in vitro to target cells that are deficient in that particular gene.

In an alternate embodiment, the conjugate may be designed so that the compound is delivered to the target but not released. Thus, the present invention may also be used for locating, detecting, and quantitating specific sites in vivo and in vitro such as tumors, organs, or sites of infection. This embodiment of the invention is particularly useful in imaging systems, cell sorting techniques, and separation schemes.

Specifically, in the case of imaging, a radiopharmaceutical or heavy metal is (a) covalently bound to the linker or (b) non-covalently bound to the linker via a chelator. Therefore, depending upon the nature of the target and purpose of delivery, a wide range of antibodies, linkers, and compounds of interest may be used in a variety of combinations.

5.1 CHOICE OF ANTIBODY AND COMPOUND OF INTEREST

According to the present invention, antibodies directed against any antigen may be used as the carrier molecules. Although conventional antibodies may be used as carrier molecules, monoclonal antibodies offer several advantages. Each monoclonal antibody is specific for one antigenic determinant, thus, when a monoclonal antibody is used as a carrier molecule the degree of non-specific binding and subsequent non-specific release of the compound is reduced. In addition, unlimited amounts of each monoclonal antibody can be produced. Thus, when using monoclonal antibodies as carrier molecules the efficiency of the delivery system is improved.

Carrier antibodies used in the present invention may be directed against any target, e.g., tumor, bacterial, fungal, viral, parasitic, mycoplasmal, histocompatibility, or differentiation antigens. When delivery and release are desired, then immunoglobulins of the IgM class or certain subclasses of IgG should be used since these are the types of immunoglobulin that are known to activate complement. In other applications carrier immunoglobulins may be used which are not capable of complement activation. Such immunoglobulin carriers may include: certain classes of antibodies such as IgA, IgD, IgE; certain subclasses of IgG; or certain fragments of immunoglobulins, e.g., half antibody molecules (a single heavy:light chain pair), or Fab, Fab', or (Fab')$_2$ fragments. When imaging of in vivo targets is to be accomplished, the use of antibody fragments as carrier is advantageous since these fragments permeate target sites at an increased rate. Additionally, a combination of antibodies reactive to different antigenic determinants may be used.

The compound used in the practice of the present invention is selected according to the purpose of the intended application (e.g., killing, prevention of cell proliferation, hormone therapy, target imaging, or gene therapy, cell sorting, or separation schemes). Such compounds may include, for example, pharmaceutical agents, toxins, fragments of toxins, alkylating agents, enzymes, antibiotics, antimetabolites, antiproliferative agents, hormones, neurotransmitters, DNA, radioopaque dyes, radioactive isotopes, fluorogenic compounds, marker compounds, lectins, compounds which alter cell membrane permeability, and insoluble matrices. Table I lists some of the pharmaceutical agents that may be employed in the herein described invention and in no way is meant to be an exhaustive list. Finally, a combination of compounds may be used.

5.2 SERUM COMPLEMENT AND SELECTION OF LINKERS

Figure 1A:
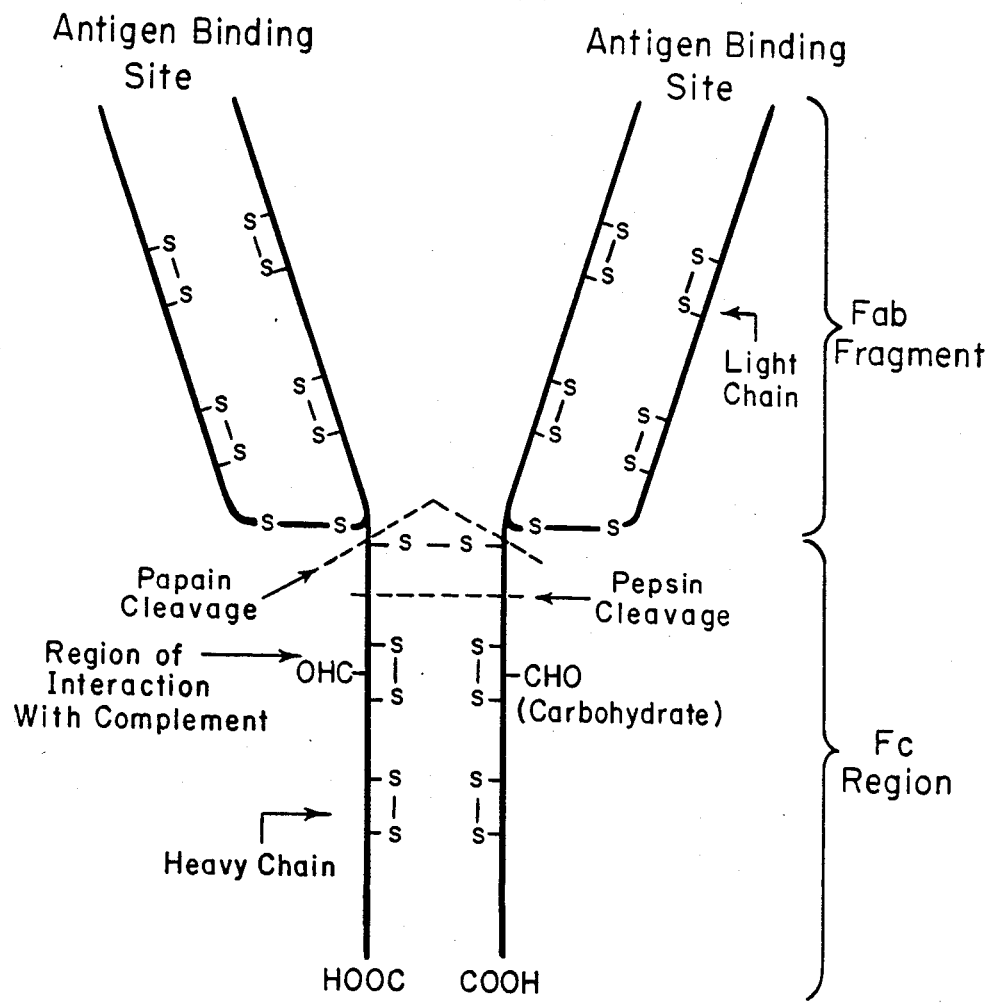
Figure 1B:
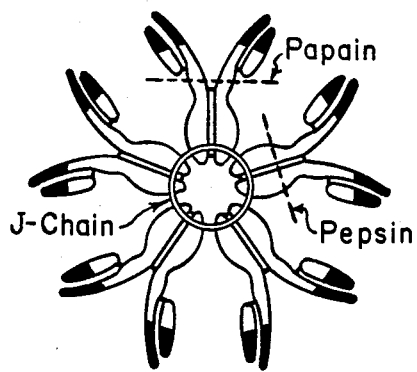

According to the method of the present invention, when release of a compound is desired, that compound is linked to a specific site on an antibody of the IgM class or certain subclasses of IgG (FIG. 1). The resulting conjugate retains the ability to bind antigen and activate the complement cascade.

Complement is the collective name for a group of serum proteins which can be activated in one of two ways, the classical pathway and the properdin pathway (Müller-Eberhard Hospital Practice, August 1977: 33–43). The classical pathway is initiated by the binding of antibodies of the IgM class or certain subclasses of IgG to its corresponding antigen whereas the properdin pathway is dependent upon the serum protein, properdin and other non-immunoglobulin serum factors (Reid and Porter, 1981, Ann. Rev. Biochem. 50: 433–464).

Figure 2:
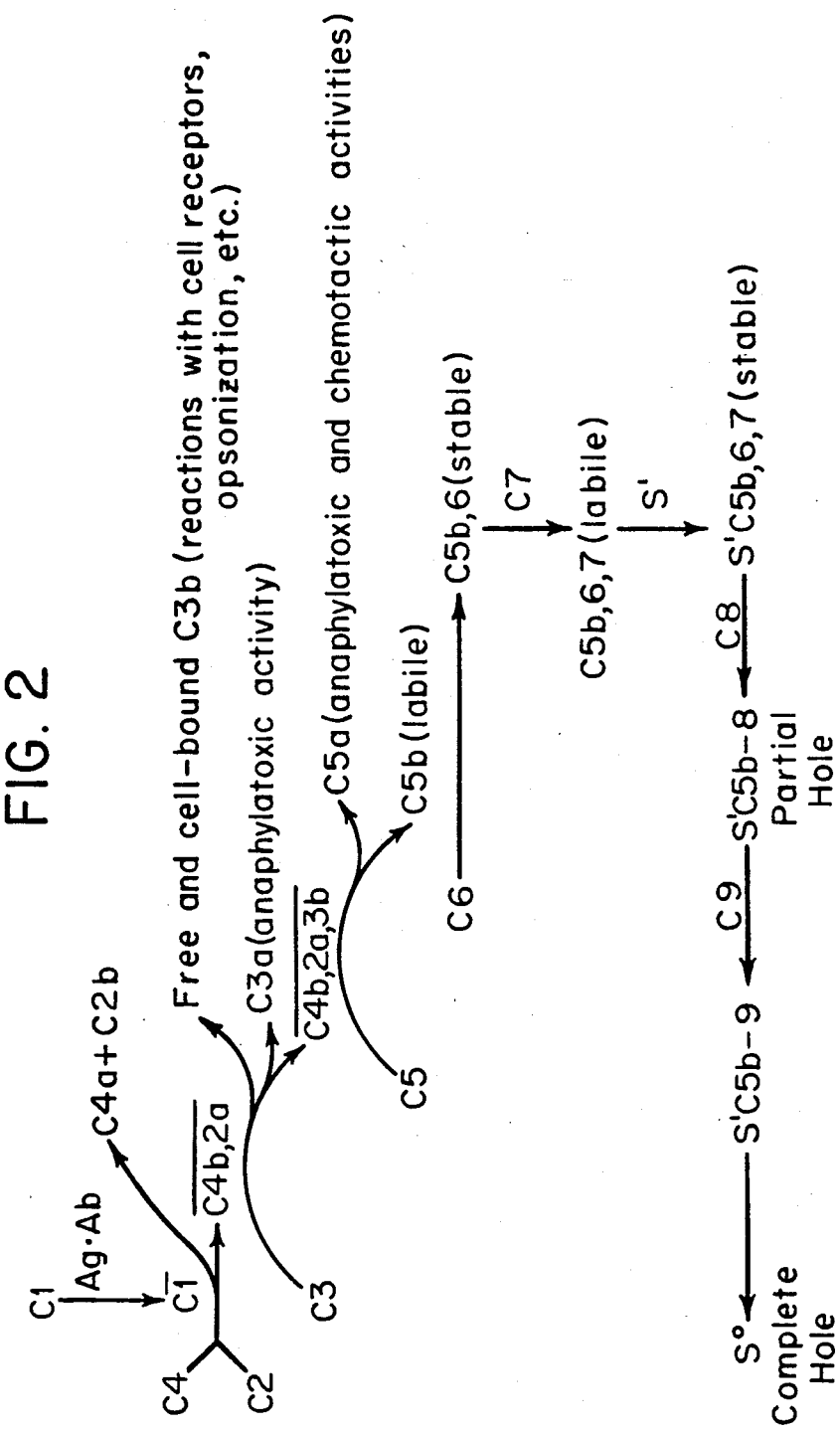

The classical pathway is the pathway of particular importance for the practice of the present invention. The classical pathway is characterized by the formation of certain antibody-antigen complexes (or immune complexes) which activate the proteolytic enzymes of the complement system (Borsos and Rapp, 1965, J. Immunol. 95: 559–566; Cohen, 1968, J. Immunol. 100: 407–413; Cohen and Becker, 1968, J. Immunol. 100: 403–406; Ishizaka et al., 1968, J. Immunol. 100: 1145–1153). These activated complement enzymes cleave and activate other components of the complement cascade (FIG. 2). Ultimately the formation of an "attack complex" (or lytic complex) is induced resulting in disruption of target cell membrane integrity.

TABLE I

DRUGS FOR ANTIBODY-MEDIATED DELIVERY

| TYPE | NAME/CLASS | LINKAGE | MANUFACTURER(S) |
|---|---|---|---|
| Antibacterials | Aminoglycosides | | |
| | Streptomycin | ester/amide | |
| | Neomycin | ester/amide | Dow, Lilly, Dome, Pfipharmics |
| | Kanamycin | ester/amide | Bristol |
| | Amikacin | ester | Bristol |
| | Gentamicin | ester/amide | Upjohn, Wyeth, Schering |
| | Tobramycin | ester/amide | Lilly |
| | Streptomycin B | ester/amide | Squibb |
| | Spectinomycin | ester | Upjohn |
| | Ampicillin | amide | Squibb, Parke-Davis, Comer, Wyeth, Upjohn, Bristol, SKF |
| | Sulfanilamide | amide | Merrell-National |
| | Polymyxin | amide | Burroughs-Wellcome, Dow, Parke-Davis |
| | Chloramphenicol | ester | Parke-Davis |
| Antivirals | Acyclovir | | Burroughs-Wellcome |
| | Vira A | ester/amide | Parke-Davis |
| | Symmetrel | amide | Endo |
| Antifungals | Nystatin | ester | Squibb, Primo, Lederle, Pfizer, Holland-Rantos |
| Antineoplastics | Adriamycin | ester/amide | Adria |
| | Cerubidine | ester/amide | Ives |
| | Bleomycin | ester/amide | Bristol |
| | Alkeran | amide | Burroughs-Wellcome |
| | Valban | ester | Lilly |
| | Oncovin | ester | Lilly |
| | Fluorouracil | ester | Adria, Roche, Herbert |
| Radiopharmaceuticals | I$^{125}$ | | |
| | I$^{131}$ | | |
| | $^{99m}$Tc (Technetium) | | |
| Heavy Metals | Barium | | |
| | Gold | | |
| | Platinum | | |
| Antimycoplasmals | Tylosine | | |
| | Spectinomycin | | |

The first component activated in the classical pathway is C1 which becomes a protease that acts on both C2 and C4. Activated C1 ($\overline{C1}$) has a specific esterase activity. Activated C4,2 ($\overline{C4_b,2_a}$), sometimes called C3 convertase, is a complex which proteolytically cleaves C3, and together with activated C3, cleaves C5. Cleavage of C3 is the first step in common between the classical and properdin pathways of complement activation.

The enzymatic activities of both $\overline{C1}$ and $\overline{C4_b,2_a}$ have been recently studied using model synthetic substrates (see Table II) which are cleaved at the carboxy terminal ester or amide bond in vitro. These synthetic substrates may be used as linkers between an antibody molecule and a compound as described in the present invention. Such linkers will allow for the specific complement mediated cleavage and subsequent release of the compound in its active form at the target site. However, any substrate which is susceptible to cleavage by any of the components of complement may be used as a linker.

Figure 3:
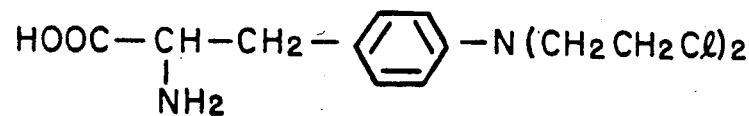
FIG. 3 depicts a general reaction scheme for the attachment of the antineoplastic drug, Alkeran (Burroughs-Wellcome), to the peptide CBZ-gly-gly-arg.
Figure 3:
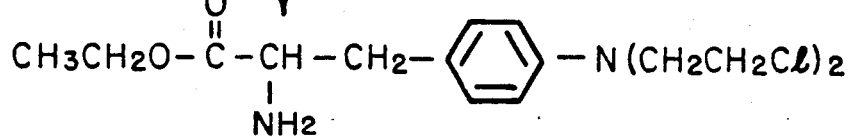
Figure 3:
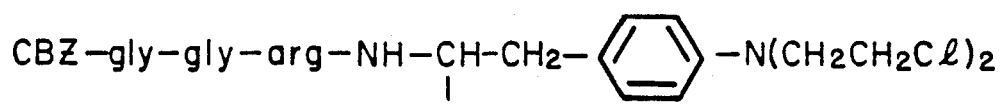
Figure 3:
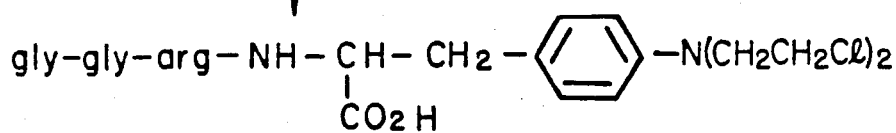

Thus, according to the present invention, a compound is joined to one end of the substrate linker group and the other end of the linker group is attached to a specific site on the antibody molecule. For example, if the compound has an hydroxy group or an amino group, the compound may be attached to the carboxy terminus of a peptide, amino acid or other suitably chosen linker via an ester or amide bond, respectively. For example, such compounds may be attached to the linker peptide via a carbodiimide reaction. If the compound contains functional groups that would interfere with attachment to the linker, these interfering functional groups can be blocked before attachment of the compound and deblocked once the conjugate is made. For example, FIG. 3 depicts a reaction scheme for the attachment of the antineoplastic drug, Alkeran (Burroughs-Wellcome) to the peptide CBZ-gly-gly-arg. The opposite or amino terminal of the linker group is then modified for binding to an antibody molecule which is capable of activating complement.

The compound may be attached to the linker before or after the linker is attached to the antibody molecule. In certain applications such as attachment of short-lived radioisotopes to antibodies, it is desirable to first produce a stable modified antibody as an intermediate wherein the linker is free of an associated compound. Depending upon the particular application, the compound may be covalently attached to the linker of the modified antibody. These peptide linkers may be variable in length since distance of the substrate from the antibody molecule may affect efficiency of cleavage which occurs at the amide or ester bond between the linker and the compound. These linkers may also include organic compounds, for example, organic polymers of any desired length, one end of which can be covalently attached to specific sites on the antibody molecule. The other end of the organic polymer may be attached to an amino acid or peptide linker. Table III lists other substrates that may be used as linker groups to prepare the antibody conjugates of the present invention. (In the table n may be an integer including zero.) These sequences were derived from those of the complement substrate sequences by substituting amino acids with similar acid-base properties. This list is not exhaustive.

Thus when these conjugates bind to antigen in the presence of complement the amide or ester bond which attaches the compound to the linker will be cleaved, resulting in release of the compound in its active form.

These conjugates, when administered to an individual, will accomplish delivery and release of the compound at the target site, and are particularly effective for the in vivo delivery of pharmaceutical agents, antibiotics, antimetabolites, antiproliferative agents, and cytotoxins.

In an alternate embodiment the conjugates of the present invention may be used to detect the target antigen in vitro. For instance, if the conjugate is added to a test mixture containing the target antigen and serum complement, the resulting complement mediated release of the compound (e.g., a fluorescent compound) is an indication and measure of the presence of target antigen in the test mixture.

TABLE II

SYNTHETIC SUBSTRATES FOR COMPLEMENT COMPONENTS

| | Reference No.* |
|---|---|
| For $\overline{C1}$: | |
| N—Boc—tyrosine o-nitrophenyl ester | 1 |
| N—Boc—phenylalanine o-nitrophenyl ester | 1 |
| α-N—Boc—lysine o-nitrophenyl ester | 1 |
| N—CBZ—tyrosine p-nitrophenyl ester | 2 |
| For $\overline{C4_b,2_a}$: | |
| N—acetyl-gly-lys-methyl ester | 3 |
| α-N—CBZ—lys-methyl ester | 3 |
| α-N—acetyl-lys-methyl ester | 3 |
| Boc—leu-gly-arg-7-amino-4-methylcoumarin | 4 |

*1. Sim, et al., 1977, Biochem. J. 163:219-27.
2. Bing, 1969, Biochemistry 8:4503-10.
3. Cooper, N. R., 1975, Biochemistry 14:4245-51.
4. Caporale, et al., 1981, J. Immunol. 128:1963-65.

TABLE III

LINKER GROUPS FOR ATTACHMENT OF COMPOUNDS OF INTEREST (CI) TO ANTIBODY MOLECULES[1]

A. Linkers For Cleavage by $\overline{C1}$

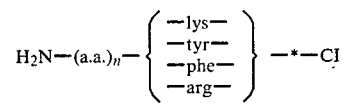

B. Tripeptide Sequences For Cleavage by $\overline{C4_b,2_a}$

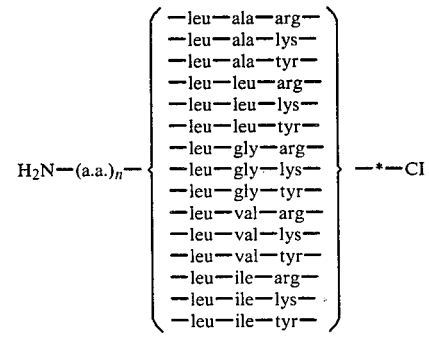

TABLE III-continued

LINKER GROUPS FOR ATTACHMENT OF COMPOUNDS OF INTEREST (CI) TO ANTIBODY MOLECULES[1]

III B.

$$H_2N-(a.a.)_n-\left\{\begin{array}{l}-ala-ala-arg-\\-ala-ala-lys-\\-ala-ala-tyr-\\-ala-leu-arg-\\-ala-leu-lys-\\-ala-leu-tyr-\\-ala-gly-arg-\\-ala-gly-lys-\\-ala-gly-tyr-\\-ala-val-arg-\\-ala-val-lys-\\-ala-val-tyr-\\-ala-ile-arg-\\-ala-ile-lys-\\-ala-ile-tyr-\end{array}\right\}-*-CI$$

$$H_2N-(a.a.)_n-\left\{\begin{array}{l}-gly-ala-arg-\\-gly-ala-lys-\\-gly-ala-tyr-\\-gly-leu-arg-\\-gly-leu-tyr-\\-gly-leu-lys-\\-gly-gly-arg-\\-gly-gly-lys-\\-gly-gly-tyr-\\-gly-val-arg-\\-gly-val-lys-\\-gly-val-tyr-\\-gly-ile-arg-\\-gly-ile-lys-\\-gly-ile-tyr-\end{array}\right\}-*-CI$$

$$H_2N-(a.a.)_n-\left\{\begin{array}{l}-val-ala-arg-\\-val-ala-lys-\\-val-ala-tyr-\\-val-leu-arg-\\-val-leu-lys-\\-val-leu-tyr-\\-val-gly-arg-\\-val-gly-lys-\\-val-gly-tyr-\\-val-val-arg-\\-val-val-lys-\\-val-val-tyr-\\-val-ile-arg-\\-val-ile-lys-\\-val-ile-tyr-\end{array}\right\}-*-CI$$

$$H_2N(a.a.)_n-\left\{\begin{array}{l}-ile-ala-arg-\\-ile-ala-lys-\\-ile-ala-tyr-\\-ile-leu-arg-\\-ile-leu-lys-\\-ile-leu-tyr-\\-ile-gly-arg-\\-ile-gly-lys-\\-ile-gly-tyr-\\-ile-val-arg-\\-ile-val-lys-\\-ile-val-tyr-\\-ile-ile-arg-\\-ile-ile-lys-\\-ile-ile-tyr-\end{array}\right\}-*-CI$$

III C. Peptide Sequences for Cleavage by $\overline{C4_b,2_a}$

TABLE III-continued

LINKER GROUPS FOR ATTACHMENT OF COMPOUNDS OF INTEREST (CI) TO ANTIBODY MOLECULES[1]

$$H_2N-\left\{\begin{array}{l}-leu-gly-\\-leu-leu-\\-leu-ala-\\-leu-val-\\-leu-ile-\\-gly-gly-\\-gly-leu-\\-gly-ala-\\-gly-val-\\-gly-ile-\\-ala-gly-\\-ala-leu-\\-ala-ala-\\-ala-val-\\-ala-ile-\\-val-gly-\\-val-leu-\\-val-ala-\\-val-val-\\-val-ile-\\-ile-gly-\\-ile-leu-\\-ile-ala-\\-ile-val-\\-ile-ile-\end{array}\right\}-\text{Tripeptide}^2-*-CI$$

[1]The asterisk (*) represents either an amide bond (Linker—C—NH—CI) or an ester bond (Linker—C—O—CI).
[2]Tripeptide represents any of the Tripeptides listed in Table III B.

In certain applications, release of the compound is not desirable. Thus, under an alternate embodiment of the present invention a compound is attached to antibody molecules via linkers which are not susceptible to cleavage by complement enzymes. These linkers may include amino acids, peptides, or other organic compounds which may be modified to include functional groups that can subsequently be utilized in attachment to antibody molecules or antibody fragments by the methods described herein. A general formula for such an organic linker is $$W-(CH_2)_n-Q$$

wherein,
W is either —NH—CH$_2$— or —CH$_2$—;
Q is an amino acid, peptide, chelator, chelator derivative (e.g., diethylenetriaminepentaacetic acid); and
n is an integer from 0 to 20.

Alternatively, a compound may be attached to antibody molecules or antibody fragments which do not activate complement. When using carrier antibodies that are incapable of complement activation, this attachment may be accomplished using linkers that are susceptible to cleavage by activated complement or using linkers that are not susceptible to cleavage by activated complement. The non-cleavage approach may be used to attach antibody molecules or fragments to immobilized or insoluble matrices, e.g., agarose, polyacrylamide, etc. These products may then be used to identify or separate specific antigenic components from complex mixtures. This technique may be accomplished by allowing a mixture which is suspected to contain antigen to contact the immobilized antibody conjugates. After washing off all nonreacting components, the target antigen may be removed from the insoluble matrix by treatment with a denaturant or chaotropic agent that is capable of dissociating antigen-antibody complexes.

This non-cleavage approach is also particularly useful for making antibody conjugates for use in cell sorting techniques (Loken and Herzenberg, 1975, Annals N.Y. Acad. Sci. 254: 163-171) and in imaging systems for locating tumors, organs, sites of infection, etc., where release of the compound is *not* desirable. In such imaging systems, the use of antibody fragments offers a distinct advantage since such fragments diffuse and permeate tissue masses more easily than do whole antibody molecules. In addition, antibody fragments do not cross placental barriers (Bellanti, 1978, Immunology II. W. B. Saunders, Philadelphia). Therefore, tumor imaging may be practiced in pregnant females.

In still another embodiment, it may be necessary to construct the linker in such a way as to optimize the spacing between the compound and the antibody. This may be accomplished by use of a linker of the general structure

W—(CH$_2$)$_n$—Q wherein Q is an amino acid or peptide and W and n are as described above.

In yet another application of target delivery, a release of the compound without complement application is desired since activation of the complement cascade will ultimately lyse the target cell. Hence, this approach is useful when delivery and release of the compound should be accomplished without killing the target cell. Such is the goal when delivery of cell mediators such as hormones, enzymes, corticosteroids, neurotransmitters, genes or enzymes to target cells is desired. These conjugates may be prepared by attaching the compound to an antibody molecule or fragment that is not capable of activating complement via a linker that is mildy susceptible to cleavage by serum proteases. When this conjugate is administered to an individual, antigen-antibody complexes will form quickly whereas cleavage of the compound will occur slowly, thus resulting in release of the compound at the target site.

5.3 METHODS FOR ATTACHING COMPOUNDS TO ANTIBODY MOLECULES

The first steps in activation of the classical complement pathway require an interaction between C1 and antibody-antigen complexes. This interaction requires that a site in the Fc region of the antibody molecule be present (FIG. 1). The present invention describes the attachment of a substrate-linker to an antibody so that the resulting antibody conjugates retain the ability to bind antigen and activate complement. In selected applications, this promotes the release of the compound in its active form at the target site. Several approaches and sites of attachment are described below.

5.3.1 ATTACHMENT TO OXIDIZED CARBOHYDRATE MOIETIES OF THE ANTIBODY MOLECULE

Glycoproteins are one of several types of biologically important macromolecules which have found application in selected therapeutic and/or diagnostic settings. These compounds share the structural characteristics which include carbohydrate residues which are covalently attached to a polypeptide backbone. Although the currently recognized classes of glycoproteins are far from complete, a catalog of such materials would include immunoglobulins, serum complement components, a variety of enzymes, cell surface histocompatibility antigens and cell surface receptors.

Since antibodies are glycoproteins, compounds may be attached to the carbohydrate moiety of the molecule. Some of the carbohydrate moieties are located on the Fc region of the immunoglobulin which are required in order for C1 binding to occur. Removal of the carbohydrate moiety results in loss of the ability of the immune complex to bind component C1 of complement (Winkelhake et al., 1980, J. Biol. Chem. 255: 2822-2828). The Fab or Fab' fragments of any immunoglobulins which contain carbohydrate moieties may be utilized in the reaction scheme described herein. An example of such an immunoglobulin is the human IgM sequenced by Putnam, et al. (1973, Science 182:287).

As explained in the present invention, these carbohydrate side chains may be selectively oxidized; for example, with galactose oxidase or periodate used as a mild oxidizing agent to generate aldehydes. The resulting aldehydes may then be reacted with amine groups (e.g., ammonia derivatives such as hydroxylamine, hydrazine, phenylhydrazine, or semicarbazide) to form a Schiff base (e.g., oxime, hydrazone, phenylhydrazone or semicarbazone, respectively).

Accordingly the substrate linkers are modified by attaching hydrazine or hydrazide deriviatives to one end of the linker. The unmodified sites on the linker may or may not be covalently attached to a compound. For instance, the substrate linkers which are attached to a compound via an ester or amide link, as described in Section 5.2 (see Table II and Table III) are modified by attaching a hydrazide (e.g., phenylhydrazine) to the opposite amino terminus of the peptide chain. This results in the following structure (N.B., the symbol * signifies an amide or ester bond):

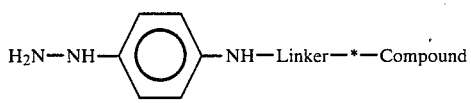

H$_2$N—NH—⟨○⟩—NH—Linker—*—Compound

Although in the structure shown the hydrazine is in the para position, one could alternatively use compounds with the hydrazine moiety in the ortho or meta positions. These hydrazide derivatives of the peptide linkers which are attached to a compound via an ester or amide link are then reacted with an oxidized immunoglobulin, or immunoglobulin fragment containing an oxidized carbohydrate. This results in hydrazone formation and the covalent attachment of the compound to the carbohydrate side chain of the immunoglobulin via a linker group which is susceptible to cleavage by complement. If desired, the linker utilized may be resistant to cleavage by either activated complement or serum proteases (e.g. a linker which includes a chelator or chelator derivative for use in an imaging system). In another application the linker may be designed to be susceptible to cleavage by a serum protease. The covalent attachment of the linker to the carrier antibody as described herein does not interfere with the antigen binding site of the molecule nor with complement fixation. The resulting structure is schematically represented below (N.B., the symbol * signifies an amide or ester bond):

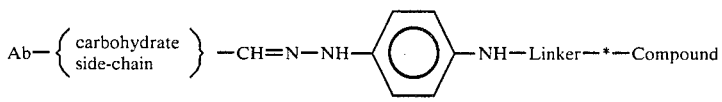

Although this section is directed primarily to reactions with the carbohydrate moieties of antibodies, such techniques are applicable to other classes of glycoproteins as well.

5.3.2 ATTACHMENT TO SULFHYDRYL GROUPS OF THE ANTIBODY MOLECULE

Free sulfhydryl groups can be generated from the disulfide bonds of the immunoglobulin molecule. This is accomplished by mild reduction of the antibody molecule. The disulfide bonds of IgG which are generally most susceptible to reduction are those that link the two heavy chains. The disulfide bonds located near the antigen binding region of the antibody molecule remain relatively unaffected (see FIG. 1). Such reduction results in the loss of ability to fix complement but does not interfere with antibody-antigen binding ability (Karush et al., 1979, Biochem. 18: 2226-2232). The free sulfhydryl groups generated in the intra-heavy chain region can then react with iodoalkyl derivatives of any compound containing carboxy or amino groups (e.g., iodoalkyl derivatives of linker groups which are attached to a compound) to form a covalent linkage. Such linkage does *not* interfere with the antigen binding site of the immunoglobulin.

Antibody conjugates which are produced by attaching a compound to free sulfhydryl groups of reduced immunoglobulin or reduced antibody fragments do not activate complement. Thus, these conjugates may be used for in vitro separation or in vivo imaging systems where cleavage and release of the compound is not desirable. Such conjugates may also be used when non-complement mediated release is desired. In such an embodiment, the compound may be linked to sulfhydryls on the reduced immunoglobulin, or reduced antibody fragments via linkers which are susceptible to cleavage by serum proteases.

The Fab' fragments of IgG immunoglobulins are obtained by cleaving the antibody molecule with pepsin (resulting in a bivalent fragment, (Fab')$_2$) or with papain (resulting in 2 univalent fragments, 2 Fab); see FIG. 1. The Fab and (Fab')$_2$ fragments are smaller than a whole antibody molecule and, therefore, permeate the target site or tissue more easily. This offers a distinct advantage for in vivo imaging since conjugates will more readily penetrate in vivo sites (e.g., tumor masses, infection sites, etc.). An additional advantage is obtained when using conjugates formed with antibody fragments because these fragments do not cross a placental barrier. As a result, using this embodiment of the invention, an in vivo site (such as a tumor) may be imaged in a pregnant female without exposing the fetus to the imaging compound.

Although attachment of a compound to sulfhydryl groups of the antibody molecule destroys complement fixation ability, such methods of attachment may be used to make antibody conjugates for use in the complement mediated release system. In such an embodiment, a compound joined to a complement sensitive substrate linker can be attached to sulfhydryls of reduced Ig molecules or antibody fragments and delivered to the target in a mixture with intact antibody molecules that are capable of activating complement. The latter would activate complement which would cleave the compound from the former. The use of antibody fragments as carrier molecules in the complement mediated release system would permit the treatment of pregnant females, and offers the advantage of more rapid penetration of the conjugate into target sites.

According to the present invention, for attachment to sulfhydryl groups of reduced antibody molecules, the substrate linkers are modified by attaching an iodoalkyl group to one end of the linker. The unmodified site on the linker may or may not be covalently attached to a compound. For instance, the substrate linkers which are ester or amide linked to compounds as prepared in Section 5.2 (see Table II and Table III) are modified by the addition of an iodoalkyl group thus forming an iodoalkyl derivatives as depicted below (N.B. the symbol * signifies an amide or ester bond):

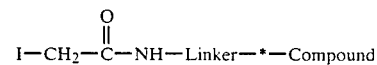

As mentioned previously the linker may be one that is susceptible or resistant to cleavage by activated complement, or serum proteases.

When the iodoalkyl derivatives of the linker group are reacted with reduced antibody molecules or reduced antibody fragments, the linker group becomes covalently attached to the antibody molecules or fragment. This is depicted below (N.B. the symbol * signifies an amide or ester bond):

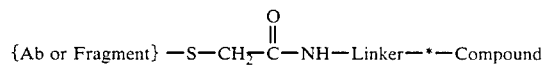

5.3.3 ATTACHMENT TO AMINO OR CARBOXY GROUPS OF THE Fc REGION OF THE ANTIBODY MOLECULE

A modification of conventional methods for linking compounds to antibody molecules may also be used for the purposes of the present invention. These conventional methods attach compounds to amino or carboxy groups of the antibody molecule. A disadvantage of conventional methods is a decreased binding affinity of the antibody molecule for antigen (i.e., a decreased immunospecific activity) because of non-specific binding of the linkers or compounds to the Fab region (antigen binding arms) of the antibody molecule. Thus, in order to utilize conventional linking methods, the substrate linker should be directed to a more optimal position on the antibody molecule to allow immune complex formation and cleavage by complement. To this end, the antigen-binding arms (Fab regions) of the immunoglobulin or half-molecules are protected while either the amino or carboxy groups of the Fc region are reacted with a substrate linker, for example, via a soluble carbodiimide reaction. If the linker is covalently attached to a compound, any reactive groups in the compound which could interfere with binding to the antibody molecule should be blocked before reacting the antibody molecule with the linker. Once the antibody conjugate is formed, the groups on the compound can be deblocked. The linker may be susceptible or resistant to cleavage by activated complement, or serum proteases. The extent of coupling can be controlled by limiting reagents. For instance (N.B. the symbol * signifies an amide or ester bond):

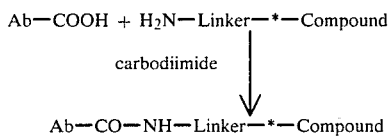

Protection of the Fab arms may be accomplished in a number of ways. The Fab portion of the carrier antibody molecule may be bound to antibodies directed against the carrier Fab antigen binding arms (anti-Fab-antibodies). Subsequent linking reactions will result in attachment of the compound to the unbound Fc portion of the carrier antibody molecules. The anti-Fab-antibody may be immobilized on a column to allow ease in separation of reacted and unreacted components.

Such a conjugate may be prepared as follows (wash thoroughly with buffer after each step of the procedure): attach the anti-Fab-antibody to an appropriate support matrix such as a cyanogen bromide activated Sepharose column. Load the column with carrier antibody so that all antigen-binding sites on the column are saturated. The Fab region of the carrier antibody is now bound and protects the antigen combining sites on the anti-Fab-antibody. Treat the column with an amino group blocking agent (e.g., acetic anhydride, carbobenzoxy chloride, etc.) in order to block all free amino groups on the exposed portions of both the anti-Fab-antibody and the bound carrier antibody. The column is then washed with a chaotropic agent (e.g., thiocyanate, perchlorate, iodide, etc.) or a denaturing agent (e.g., urea, formol-urea, guanidine hydrochloride, etc.) which dissociates the carrier antibody from the anti-Fab-antibody without destroying the immunospecific activity of the anti-Fab-antibody (Dandliker et al., 1967, Biochemistry 6(5): 1460–1467). This treatment releases the carrier antibody molecules which are discarded, leaving the immobilized anti-Fab-antibody free to form subsequent immune complexes. The column, which now consists of immobilized anti-Fab-antibody, containing blocked amino groups in the non-antigen binding sites, is loaded with carrier antibody. After the carrier antibody binds to the anti-Fab-antibody, the conventional linkage reaction is carried out using a substrate linker attached to a compound. Since the only available amino groups are on the Fc portion of the carrier antibody this reaction results in attachment of the compound via the substrate linker to this portion of the carrier antibody. Finally, the resulting conjugate is released from the column by elution with an appropriate buffer (e.g., chaotropic agent or denaturant).

6. EXAMPLES: A METHOD FOR COMPLEMENT-MEDIATED RELEASE OF ANTIBODY-TARGETED COMPOUNDS AT CELL SURFACES

The following examples illustrate a method for the specific attachment to an antibody molecule of a peptide linked to a compound of interest (compound) via an amide or ester bond. The resulting antibody conjugate retains the ability to fix complement as revealed by a hemolytic complement fixation assay. Furthermore, the specific release of the compound at the antigenic cell surface via enzymatic cleavage by the complement system is demonstrated by a non-hemolytic assay.

In the following examples the compound is fluorogenic. Thus, the complement mediated release of the fluorescent compound may be detected by an assay capable of differentiating between the bound and free forms of the fluorescent molecule.

6.1 OXIDATION OF THE CARBOHYDRATE MOIETY OF THE ANTIBODY MOLECULE

The antibody molecule used in this example was a monoclonal IgM (designated no. 171) specific for antigenic determinants on sheep red blood cells. To prepare the monoclonal antibody, Lewis rats were immunized with a single injection of sheep red blood cells. Three days later, spleen cells from the immunized rats were harvested and fused with the myeloma line SP2/0 Ag14 according to the method of McKearn et al., 1979, Immunol. Rev. 47:91–115. Cloned cells were then grown and the resulting monoclonal antibody was purified as described by Klinman and McKearn, 1981, J. Immunol. Methods 42:1–9.

In the presence of sheep red blood cells and serum complement, this monoclonal antibody activates the complement enzyme cascade (a result of antigen-antibody binding). Complement fixation causes lysis of the sheep red blood cells which results in the release of hemoglobin. The released hemoglobin may be detected spectrophotometrically, thus providing an assay for complement fixation.

Figure 4A:
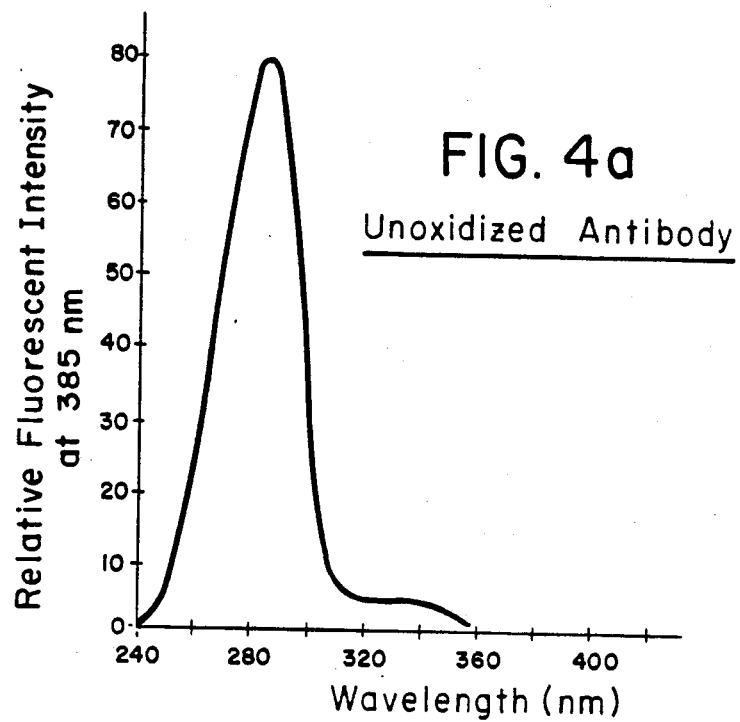
FIG. 4 represents the excitation spectra for unmodified and oxidized antibody.
Figure 4B:
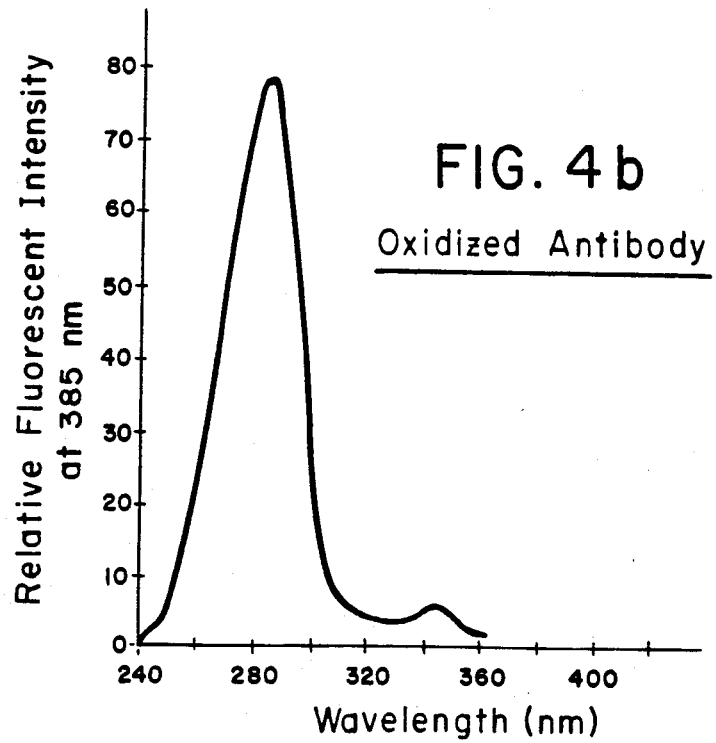

Oxidation of the antibody carbohydrate moiety was accomplished by reacting the antibody with galactose oxidase by a modification of the method of Cooper et al., 1959, J. Biol. Chem. 234: 445–448. To this end 3.8 mg of no. 171 monoclonal antibody was added to 1 ml of buffer consisting of 0.135M NaCl, 0.015M Tris-HCl (pH 7.0), 0.5 mM $MgCl_2$, and 0.15 mM $CaCl_2$. Subsequently, a 0.1 ml aliquot of a solution of galactose oxidase (Worthington Biochemical Co., Freehold, N.J.) at a concentration of 52 units of enzyme/ml of the same buffer was added to the antibody solution. Finally, 43 ug of catalase (Worthington Biochemical Co., Freehold, N.J.) dissolved in an additional 0.1 ml of the same buffer was added to the reaction mixture (the catalase was added to degrade $H_2O_2$ that is generated during the oxidation reaction). The reaction mixture was incubated for 48 hours at room temperature, then stored at 4° C. FIG. 4 represents the excitation spectra for unmodified and oxidized antibodies.

6.2 PREPARATION OF THE TRIPEPTIDE-AMC FOR ATTACHMENT TO THE ANTIBODY MOLECULE

For the purposes of the present examples, a synthetic fluorogenic compound was utilized as the peptide-linked compound. The properties of this synthetic compound are such that the bound and free states of the fluorogenic compound are spectrofluorometrically distinguishable. This provides a definitive assay for measuring the complement fixation ability of the antibody conjugate. More importantly, it provides a means for quantitating the subsequent complement-mediated release of the compound. The synthetic fluorogenic compound used was obtained from Serva Fine Biochemicals, Inc., Garden City Park, L.I., N.Y. (Catalogue #51474). This compound consists of a tripeptide (Gly-Gly-Arg) attached via an amide linkage to the fluorescent compound 7-amino-4-methyl coumarin (AMC); the amino group of glycine is blocked by carbobenzoxy chloride (Cbz). The structure of this compound (herein called Tripeptide-AMC) is shown below:

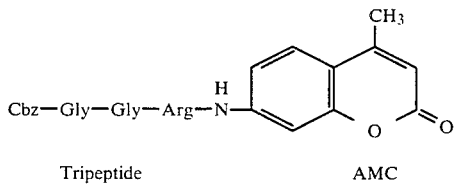

Tripeptide          AMC

The excitation and emission maxima of free AMC (345 nm and 445 nm, respectively) differ from those for AMC bound to the tripeptide (325 nm and 395 nm, respectively). This affords a means for distinguishing between the bound and free forms of the AMC molecule using a fluorometric assay. Excitation and emission wavelengths of 383 nm and 455 nm may be used for optimum differences for assay purposes; at these wavelengths, free AMC retains 20% of its maximal fluorescence but possesses a relative fluorescence 500-fold greater than an equimolar amount of bound AMC (Zimmerman et al., 1978, Proc. Natl. Acad. Sci. USA 75(2): 750-753).

In order to effect specific bonding of the Tripeptide-AMC to the oxidized carbohydrate moiety of the antibody prepared in Section 6.1, a hydrazine derivative was linked to the terminal glycine of the Tripeptide-AMC compound. The presence of the hydrazine group is advantageous since this results in reactivity for the oxidized carbohydrate moiety of the antibody molecule under very mild conditions while not affecting the antigen binding site. Aldehyde groups of the oxidized carbohydrate side chain of the antibody molecule then react with the hydrazine derivative to form a hydrazone.

In order to attach a hydrazine derivative (e.g., 4-fluorophenylhydrazine), the Tripeptide-AMC was first deblocked at the glycine amino terminus by removal of the Cbz group. This was accomplished by dissolving the Tripeptide-AMC in trifluoroacetic acid (Sigma, St. Louis, Mo.), and bubbling HBr gas (Matheson, East Rutherfurd, N.J.)through the solution for 45 minutes. The product, H$_2$N-Gly-Gly-Arg-NH-AMC, was precipitated by the addition of cold diethyl ether (Baker Chemical Co., Phillipsburg, N.J.), and dissolved in absolute ethanol (Publicker Industries Co., Linfield, Pa.). An equimolar amount of 4-fluorophenylhydrazine (Aldrich Chemical Co., Milwaukee, Wis.) in absolute ethanol was added with mixing. After incubation in the dark at room temperature for 2 hours, the reaction mixture was stored in the dark at 4° C. The resulting product (Phenylhydrazine-Tripeptide-AMC) has the structure:

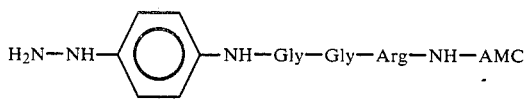

This compound was shown to be positive for fluorescence by exciting with ultraviolet light, and positive for the presence of a hydrazine group. The hydrazine linked to the tripeptide was detected by thin layer chromatography (TLC) using a spray of a 0.1% trinitrobenzene sulfonic acid aqueous solution for the colorimetric determination of a hydrazine (a pinkish color indicates the presence of hydrazine). The results of TLC demonstrated the presence of a hydrazine group at the migratory band of the Tripeptide-AMC.

Figure 5:
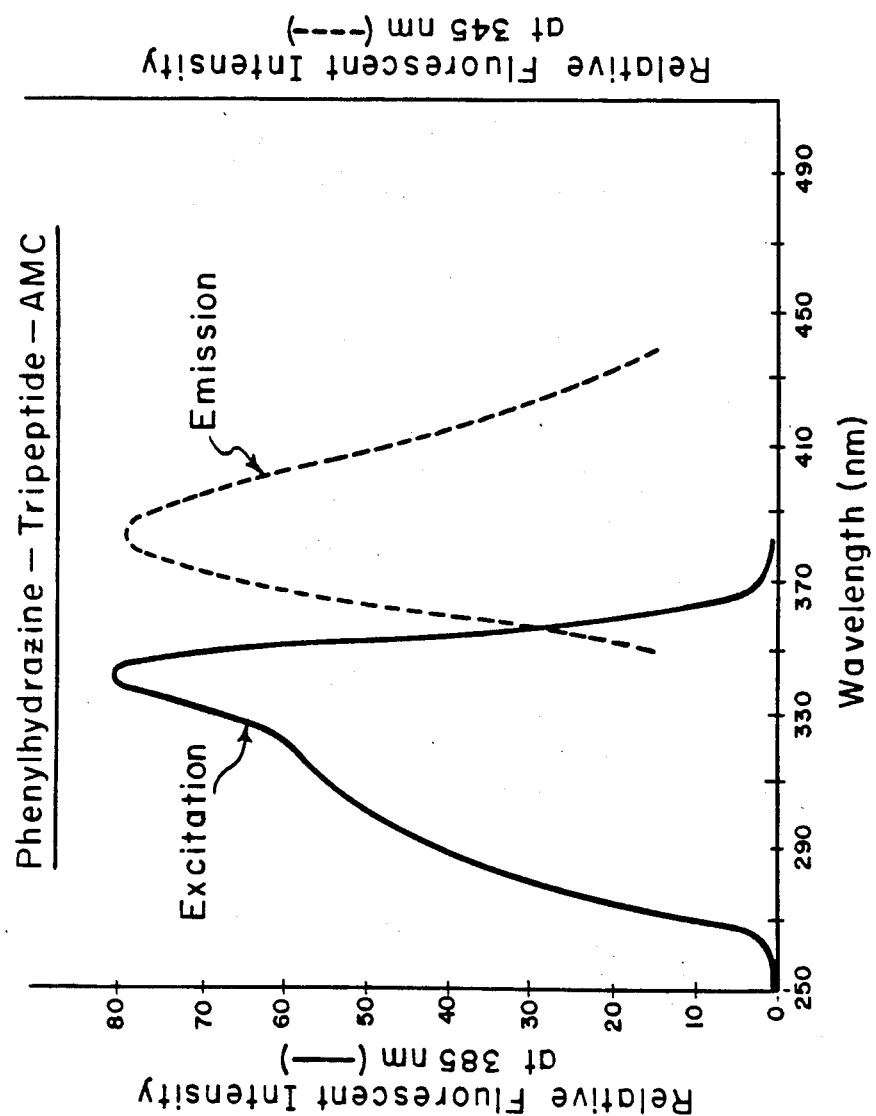
FIG. 5 represents the excitation and emission spectra of the Phenylhydrazide-Tripeptide-AMC compound.

The absorption and emission spectra for the Phenylhydrazine-Tripeptide-AMC compound as shown in FIG. 5 reveal a similarity to the Tripeptide-AMC spectra but a shift in excitation and emission maxima consistent with the covalent modification of the Tripeptide-AMC. The maxima for excitation and emission of the Phenylhydrazine-Tripeptide-AMC compound are 345 nm and 385 nm respectively. The product was precipitated from solution with cold diethyl ether, washed, and dissolved in dimethylsulfoxide (Baker Chemical Co., Phillipsburg, N.J.).

6.3 SPECIFIC COVALENT ATTACHMENT OF PHENYLHYDRAZIDE-TRIPEPTIDE-AMC TO THE OXIDIZED CARBOHYDRATE MOIETY OF THE ANTIBODY MOLECULE

The oxidized monoclonal antibody preparation, described in Section 6.1 supra, was adjusted to pH 5.1 by the addition of a small amount of 0.1M acetate buffer (pH 5.0). An estimated 10-fold excess of Phenylhydrazine-Tripeptide-AMC (prepared in Section 6.2) was added to the antibody solution, which was then incubated at 37° C. in the dark, overnight (approximately 14 hours). The reaction mixture was then chromatographed on a Sephadex G-25 column (Pharmacia Fine Chemicals, Piscataway, N.J.) in order to remove any unreacted Phenylhydrazine-Tripeptide-AMC.

Figure 6:
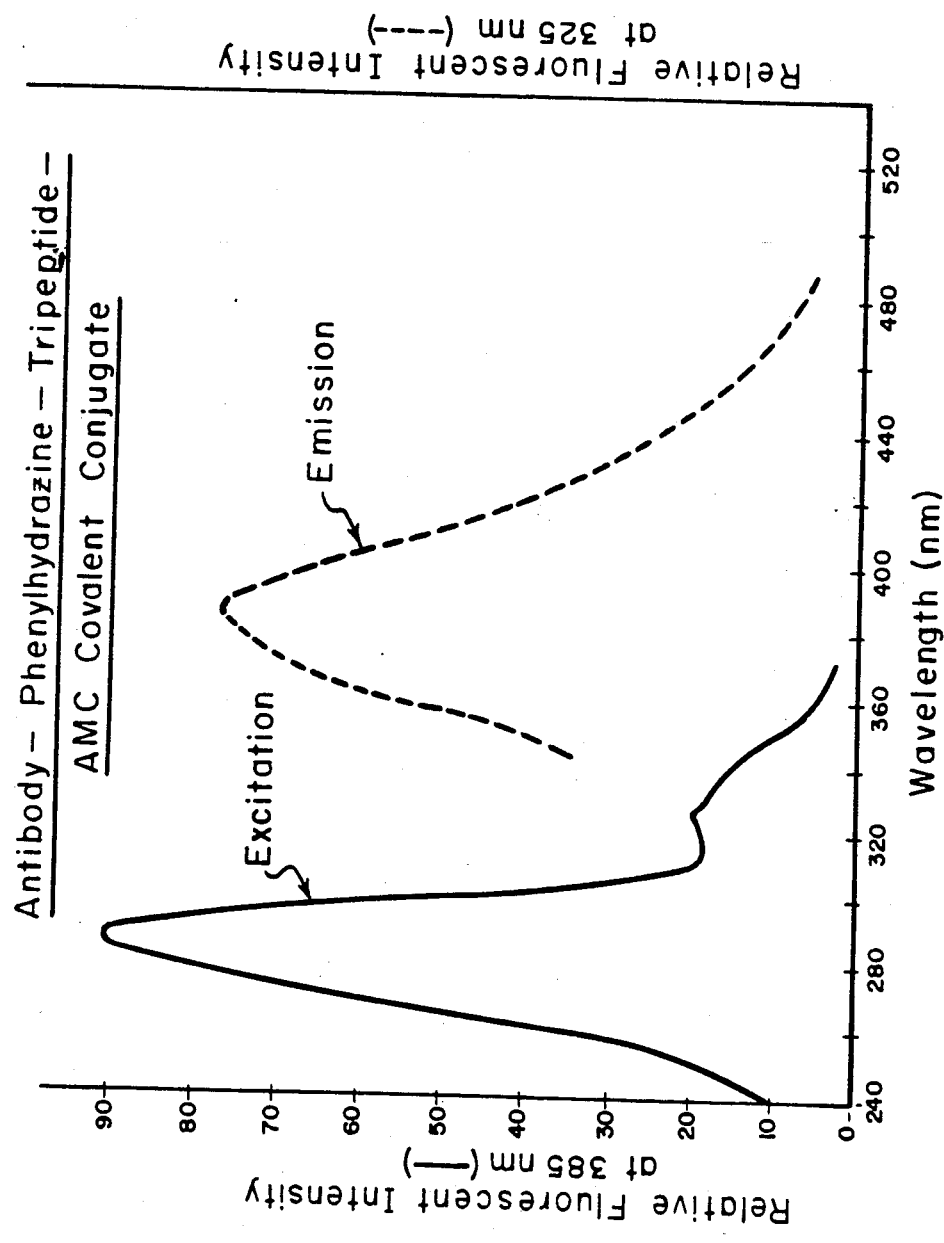
FIG. 6 represents the excitation and emission spectra of the Antibody-Phenylhydrazide-Tripeptide-AMC (APTA) covalent conjugate.

Spectrofluorometric analysis of the protein fractions confirmed the presence of the Phenylhydrazine-Tripeptide-AMC covalently attached to the antibody (now called Antibody-Phenylhydrazine-Tripeptide-AMC or conjugate). The excitation and emission maxima for the conjugate are 325 nm and 385 nm respectively (FIG. 6). The large peak at 285 nm in the excitation spectrum of the conjugate may be explained by tryptophan absorption with residual fluorescence at 385 nm and may also be the result of resonance energy transfer from the amino acid tryptophan of the antibody molecule to AMC.

6.4 COMPLEMENT FIXATION ASSAYS

Two types of complement fixation assays were utilized, hemolytic and fluorometric. These assays determined whether the Antibody-Phenylhydrazine-Tripeptide-AMC conjugate retained complement fixation ability, and whether AMC was cleaved by complement.

6.4.1 PREPARATION OF HUMAN COMPLEMENT

A 10 ml sample of freshly drawn human whole blood was clotted on ice for 17 hours. The clot was removed by centrifugation, and the resulting human serum was frozen in 0.5 ml aliquots. Human complement was shown to be active in these samples by the hemolytic assay described in Section 6.4.2.

6.4.2 HEMOLYTIC ASSAY FOR COMPLEMENT FIXATION

A 200 ul aliquot of a suspension of sheep red blood cells (Gibco Diagnostics, Madison, Wis.) at an approximate concentration of $2\times10^8$ cells/ml were mixed with 20 ul of the antibody conjugate mixture prepared in Section 6.3 (approximately 2 ug of protein). After 15 minutes of mixing and incubating at 37° C., 100 ul of the human serum complement (prepared in Section 6.4.1) was added to the mixture. After 30 min to 1 hour of incubation at 37° C., the mixture was centrifuged to pellet the cells. The extent of complement-mediated cell lysis was determined by spectrophotometrically measuring hemoglobin released into the supernatant (412 nm).

The results of this assay demonstrated complete hemolysis and essentially 100% binding of antibody to cell surface. For example, addition of distilled water to a pellet formed by centrifuging 200 ul of the sheep red blood cell suspension completely lyses the cells, and releases hemoglobin. A 1:20 dilution of the supernatant of sheep red blood cells which were completely lysed in distilled water had an $O.D._{412}$ of 0.646. An identical dilution of sheep red blood cells which were lysed by the addition of conjugate and complement had an $O.D._{412}$ of 0.672. Thus the conjugate retained the ability to bind antigen and to fix complement.

6.4.3 NON-HEMOLYTIC ASSAY FOR COMPLEMENT MEDIATED RELEASE OF AMC

Conditions for the non-hemolytic assay were identical to those above except that glutaraldehyde-fixed sheep red blood cells (Sigma, St. Louis, Mo.) were used in place of normal sheep red blood cells. Glutaraldehyde fixed cells do not lyse in the presence of antibody and complement and, therefore, no hemoglobin is released. Instead, a fluorometric assay is used to demonstrate the release of the AMC. A non-hemolytic system is necessary for use in the fluorometric assay, because the presence of hemoglobin interferes with fluorescence measurements in this system. Prior to use in the assay, these fixed red blood cells were shown to bind both the unmodified antibody and the Antibody-Phenylhydrazine-Tripeptide-AMC which was prepared in Section 6.3.

The non-hemolytic assay was used to show the specific complement-mediated release of the AMC from the antibody conjugate. Similarly to the hemolytic assay, 200 ul of the glutaraldehyde-fixed sheep red blood cells, at an approximate concentration of $2\times10^8$ cells/ml, was incubated with the Antibody-Phenylhydrazide-Tripeptide-AMC conjugate at 37° C. for 15 minutes.

After centrifuging and resuspension in buffer, 50 ul of the human complement preparation (Section 6.4.1) was added, and the fluorescense at 460 nm monitored, with excitation at 380 nm (Caporale, et al., 1981, J. Immunol. 126 1963–65.) as a function of time. As controls, the conjugate was incubated with sheep red blood cells alone; in the presence of rat red blood cells and human complement (the monoclonal antibody used does not bind to rat red blood cells); and in the absence of both sheep red blood cells and complement (the monoclonal antibody used does not bind to rat red blood cells). FIG. 7 shows the results of these experiments. A comparision of curve (a) which represents the conjugate incubated with glutaraldehyde-fixed sheep red blood cells and human complement to the control curves labeled (b), (c) and (d) clearly demonstrates the release of free AMC in the sample containing the specific antibody target and human complement. Thus, curve (b) which represents the conjugate incubated with glutaraldehyde-fixed rat red blood cells and human complement, curve (c) which represents the conjugate incubated with glutaraldehyde-fixed sheep red blood cells, and curve (d) which represents the conjugate alone demonstrate no release of AMC.

We claim:

1. A method for in vivo delivery of a compound at an antigenic site, comprising: administering to an individual an effective amount of a soluble antibody conjugate comprising an antibody or antibody fragment directed against said antigenic site and attached to a non-cleavable linker by a covalent bond to an oxidized carbohydrate moiety of the Fc region of the antibody or antibody fragment and in which such linker is covalently attached or complexed to a compound, the soluble antibody conjugate being characterized by (a) substantially the same immuno-specificity as the unconjugated antibody or antibody fragment, and (b) aqueous solubility such that the antibody conjugate is suitable for in vivo administration.

2. The method according to claim 1 wherein the covalent bond is an imine, enamine, hydrazone, oxime, phenylhydrazone, semicarbozone or reduced forms thereof.

3. The method according to claim 1, wherein the antibody fragment is selected from the group consisting of Fab fragments, (Fab')$_2$ fragments and single heavy-light chain pairs.

4. The method according to claim 1, wherein the antibody or antibody fragment is a monoclonal antibody or monoclonal antibody fragment.

5. The method according to claim 1 wherein the antigenic site is a bacterial antigen and the compound is an antibacterial agent.

6. The method according to claim 1, wherin the antigenic site is a viral antigen and the compound is an antiviral agent.

7. The method according to claim 1 wherien the antigenic site is a tumor antigen and the compound is an antitumor agent.

8. The method according to claim 7, wherein the antitumor agent is fluorouracil.

9. The method according to claim 7, wherein the antitumor agent is bleomycin.

10. The method according to claim 7, wherein the antitumor agent is methotrexate.

11. The method according to claim 7, wherein the antitumor agent is adriamycin.

12. The method according to claim 7, wherein the antitumor agent is cerubidine.

13. The method according to claim 7, wherein the antitumor agent is valban.

14. The method according to claim 7, wherein the antitumor agent is alkeran.

15. The method according to claim 1, wherein the antigenic site is a fungal antigen and the compound is an antifungal agent.

16. The method according to claim 1 wherein the antigenic site is a parasite antigen and the compound is an antiparasitic agent.

17. The method according to claim 1 wherein the antigenic site is a mycoplasmal antigen and the compound is an antimycoplasmal agent.

18. The method according to claim 1 wherein the antigenic site is a differentiation or histocompatability antigen and the compound is a cytotoxic agent.

19. The method according to claim 1 wherein the compound is a radiopharmaceutical or a heavy metal.

20. The method according to claim 19 wherein heavy metal is platinum.

21. The method according to claim 1, wherein the compound is a toxin or a toxin fragment.

22. The method according to claim 1, wherein the compound is a neurotransmitter or hormone.

23. The method of claim 1 wherein the compound is an enzyme or a DNA sequence.

24. A method for in vivo delivery and release of a compound at an antigenic site, comprising: administering to an individual an effective amount of a soluble antibody conjugate comprising an antibody or antibody fragment directed against said antigenic site and attached to a cleavable linker by a covalent bond to an oxidized carbohydrate moiety in the Fc region of the antibody or antibody fragment and in which such linker is covalently attached to a compound, the soluble antibody conjugate being characterized by (a) substantially the same immunospecificity as the unconjugate antibody or antibody fragment, (b) aqueous solubility such that the antibody conjugate is suitable for in vivo administration and (c) the linker which is unstable by reason of its ability to be cleaved by activated serum complement or a serum protease.

25. The method according to claim 24 wherein the covalent bond is an imine, enamine, hydrazone, oxime, phenylhydrazone, semicarbazone, or reduced forms thereof.

26. The method according to claim 24 wherein the antibody fragment is selected from the group consisting of Fab fragments, (Fab')$_2$ fragments and single heavy-light chain pairs.

27. The method according to claim 24 wherein the antibody or antibody fragment is a monoclonal antibody or monoclonal antibody fragment.

28. The method according to claim 24 wherein the linker is cleavable by activated C1.

29. The method according to claim 24 wherein the linker is cleavable by activated C4, 2.

30. The method according to claim 24 wherein the linker is cleavable by a serum protease.

31. The method according to claim 24 wherein the antigenic site is a bacterial antigen and the compound is an antibacterial agent.

32. The method according to claim 24 wherein the antigenic site is a viral antigen and the compound is an antiviral agent.

33. The method according to claim 24 wherein the antigenic site is a tumor antigen and the compound is an antitumor agent.

34. The method according to claim 33 wherein the antitumor agent is fluorouracil.

35. The method according to claim 33 wherein the antitumor agent is bleomycin.

36. The method according to claim 33 wherein the antitumor agent is methotrexate.

37. The method according to claim 33 wherein the antitumor agent is adraimycin.

38. The method according to claim 33 wherein the antitumor agent is cerubidine.

39. The method according to claim 33 wherein the antitumor agent is valban.

40. The method according to claim 33 wherein the antitumor agent is alkeran.

41. The method according to claim 24 wherein the antigenic site is a fungal antigen and the compound is an antifungal agent.

42. The method according to claim 24 wherein the antigenic site is a parasitic antigen and the compound is an antiparasitic agent.

43. The method according to claim 24 wherein the antigenic site is a mycoplasmal antigen and the compound is an antimycoplasmal agent.

44. The method according to claim 24 wherein the antigenic site is a differentiation or histocompatability antigen and the compound is an cytotoxic agent.

45. The method according to claim 24 wherein the compound is an radiopharmaceutical or a heavy metal.

46. The method according to claim 24 wherein the compound is an toxin or a toxin fragment.

47. The method according to claim 24 wherein the compound is a neurotransmitter or hormone.

48. The method of claim 24 wherein the compound is an enzyme or a DNA sequence.

49. A method for in vivo delivery of a compound at an antigenic site, comprising: administering to an individual an effective amount of a soluble antibody conjugate comprising an antibody or antibody fragment directed against the antigenic site and attached to a cleavable or non-cleavable liner by a covalent bond of an oxidized carbohydrate moiety of the Fc region of the antibody or of the antibody fragment and in which such linker is covalently attached or complexed to a compound, the soluble antibody conjugate being characterized by (a) substatially the same immunospecificity as the unconjugated antibody or antibody fragment, and (b) aqueous solubility such that the antibody conjugate is suitable for in vivo administration.

* * * * *

UNITED STATES PATENT AND TRADEMARK OFFICE
CERTIFICATE OF CORRECTION

PATENT NO. : 4,671,958

DATED : June 9, 1987

INVENTOR(S) : John D. Rodwell, Thomas J. McKearn

It is certified that error appears in the above-identified patent and that said Letters Patent is hereby corrected as shown below:

Title page, References cited

On page 1, correct the Karush publication by deleting "Anti-Lactive" and inserting --Anti-Lactose--; by deleting page numbers "2226-2231" and inserting --2226-2232--.

On page 1, correct the Hurwitz publication by deleting "Dainorubicin" and inserting --Daunorubicin--.

On page 1, correct the Monsigny publication by deleting "Drug-Carrier-Counter (PAC Conjugate)" and inserting --Drug-And-Carrier (DAC Conjugate)--.

On page 2, correct the Hobart publication by deleting "on the Molecular Cellular" and inserting --on the Molecular and Cellular--.

On page 2, correct the date of the Leatherbarrow publication by deleting "1983" and inserting --1985--.

Column 4, line 23 insert a "," (comma) between "fungi" and "bacteria".

Table 1 delete "Valban" and insert --Velban--.

Column 9, line 24 delete "has an hydroxy" and insert -- has a hydroxy--.

Column 21, line 59 delete "126 1963-65)" and insert --126:1963-65)--.

UNITED STATES PATENT AND TRADEMARK OFFICE
CERTIFICATE OF CORRECTION

PATENT NO. : 4,671,958

DATED : June 9, 1987

INVENTOR(S) : John D. Rodwell, Thomas J. McKearn

It is certified that error appears in the above-identified patent and that said Letters Patent is hereby corrected as shown below:

Column 22, line 28 delete "semicarbozone" and insert --semicarbazone--.

Column 22, line 40 delete "wherin" and insert --wherein--.

Column 22, line 43 delete "wherien" and insert --wherein--.

Column 22, line 57 delete "valban" and insert --velban--.

Column 23, line 24 delete "unconjugate" and insert --unconjugated--.

Column 24, line 11 delete "adraimycin" and insert --adriamycin--.

Column 24, line 15 delete "valban" and insert --velban--.

Column 24, line 29 delete "an" and insert --a--.

Column 24, line 31 delete "an" and insert --a--.

Column 24, line 33 delete "an" and insert --a--.

Column 24, line 43, delete "liner" and insert --linker--.

UNITED STATES PATENT AND TRADEMARK OFFICE
CERTIFICATE OF CORRECTION

PATENT NO. : 4,671,958

DATED : June 9, 1987

INVENTOR(S) : John D. Rodwell, Thomas J. McKearn

It is certified that error appears in the above-identified patent and that said Letters Patent is hereby corrected as shown below:

Column 24, line 48 delete "substatially" and insert

--substantially--.

Signed and Sealed this

Twelfth Day of April, 1988

Attest:

DONALD J. QUIGG

Attesting Officer

Commissioner of Patents and Trademarks